(12) United States Patent
Baumgartner

(10) Patent No.: US 7,059,060 B1
(45) Date of Patent: Jun. 13, 2006

(54) DEVICE FOR RECORDING EVENTS AND MEASURING GROWTH IN AN INDIVIDUAL'S LIFE

(76) Inventor: Daryl L. Baumgartner, 29020 Norman Ave., Wickliffe, OH (US) 44092

( * ) Notice: Subject to any disclaimer, the term of this patent is extended or adjusted under 35 U.S.C. 154(b) by 183 days.

(21) Appl. No.: 10/243,601

(22) Filed: Sep. 13, 2002

(51) Int. Cl.
*A61B 5/107* (2006.01)
*B43L 7/00* (2006.01)
*G01B 5/02* (2006.01)

(52) U.S. Cl. .............................. 33/494; 33/832; 33/512
(58) Field of Classification Search ................ 33/483, 33/485, 492–494, 832, 833, 293, 484, 679.1, 33/512, 296, 810; 368/28, 41–44, 62; 40/107, 40/109, 122, 335, 121; D10/70–71; 283/2; D19/20; 434/304

See application file for complete search history.

(56) References Cited

U.S. PATENT DOCUMENTS

| | | | | | |
|---|---|---|---|---|---|
| 34,924 | A | * | 4/1862 | Estes | 114/104 |
| 287,480 | A | * | 10/1883 | Smith | 33/483 |
| 310,513 | A | * | 1/1885 | Hoffman | 33/485 |
| 365,916 | A | * | 7/1887 | Goodrich | 40/107 |
| 865,709 | A | * | 9/1907 | Johnson | 33/485 |
| 955,114 | A | * | 4/1910 | Brooks | 24/67.11 |
| 1,226,855 | A | * | 5/1917 | Boynton | 33/833 |
| 1,457,964 | A | * | 6/1923 | Doty | 33/512 |
| 1,974,085 | A | * | 9/1934 | Shields et al. | 33/512 |
| D116,049 | S | * | 8/1939 | Noth | D10/71 |
| 2,410,696 | A | * | 11/1946 | Wheeler | 33/832 |
| D167,945 | S | * | 10/1952 | Larson | D10/71 |
| 3,137,943 | A | * | 6/1964 | Mechaneck | 33/2 R |
| 3,465,453 | A | * | 9/1969 | Sganga | 33/483 |
| 4,495,702 | A | * | 1/1985 | Bergstedt | 33/833 |
| 4,703,571 | A | * | 11/1987 | McCarthy | 40/107 |
| 5,457,902 | A | * | 10/1995 | Rubin | 40/107 |
| 5,496,070 | A | * | 3/1996 | Thompson | 40/107 |
| 5,588,215 | A | * | 12/1996 | Hart | 33/2 R |
| 5,691,932 | A | | 11/1997 | Reiner et al. | 368/10 |
| D390,871 | S | | 2/1998 | Whitney | D19/26 |
| 5,813,132 | A | * | 9/1998 | Bodkin, Sr. | 33/494 |
| 5,996,240 | A | * | 12/1999 | Casper | 33/759 |
| 6,073,359 | A | * | 6/2000 | Lee | 33/483 |
| 6,129,386 | A | * | 10/2000 | Brata | 281/5 |
| 6,226,881 | B1 | * | 5/2001 | Landauer | 33/515 |
| 6,237,239 | B1 | * | 5/2001 | Miyazaki | 33/512 |
| D444,082 | S | * | 6/2001 | Lynberg | D10/70 |
| 6,269,563 | B1 | * | 8/2001 | Dagan | 40/107 |
| 6,327,494 | B1 | * | 12/2001 | Sakai | 600/547 |
| D455,086 | S | * | 4/2002 | Chelberg | D10/70 |
| 2004/0079005 | A1 | * | 4/2004 | Davis et al. | 40/107 |

* cited by examiner

*Primary Examiner*—Christopher W. Fulton
(74) *Attorney, Agent, or Firm*—William N. Hogg

(57) ABSTRACT

A device for recording both chronological events and physical growth events of an individual or group of individuals' lives. The device includes linear measuring device having at least first and second opposed sides. The first side has a linear measurement scale inscribed thereon and at least one recording surface associated therewith. The second side has a chronological scale, preferably in months and years, inscribed thereon and also has at least one recording surface associated with the chronological scale. Thus, physical growth can be measured on the first side and recorded on the recording surface associated therewith as the individual or several individuals grow physically. Significant events can be recorded on the other side.

15 Claims, 4 Drawing Sheets

US 7,059,060 B1

DEVICE FOR RECORDING EVENTS AND MEASURING GROWTH IN AN INDIVIDUAL'S LIFE

FIELD OF THE INVENTION

This invention relates generally to a device for recording events in an individual's life and also for recording an individual's physical growth. In more particular aspects, this invention relates to a unitary device having markings and associated surfaces therewith which correspond to chronological dates and to physical measurements so that an individual's physical growth can be recorded, as well as significant events in the individual's life, on a single device.

BACKGROUND OF THE INVENTION

It has been common practice for many, many years for parents to record the physical growth of their children by having the child stand against a wall and marking the child's height and the date associated therewith on the wall or door frame. This has certain advantages in that it is essentially a permanent record, but the record stays with the wall or door frame and may either be painted over when the house is redecorated or stays with the house when the family moves to a new dwelling, which in both cases results in the loss of the records. It is also common practice for individuals to collect various mementos during their lifetime to signify important events. Such mementos include graduation tassels to signify graduation from high school, college or graduate school; mementos from their wedding; mementos from the birth of their children; and any other events which they consider significant, such as trophies they have won in various sporting events or other types of events. In the past, these have been collected in a somewhat random fashion. Often, the trophies occupy a shelf, while the other mementos are relegated to a box stored in a closet or in the attic.

In any event, it has not been conveniently possible to record in a continuous fashion both physical growth and significant life events on a single device, which can be maintained and utilized throughout the lifetime of an individual, or indeed through the collective lifetime of a family group where the physical growth and significant events of various family members are recorded.

It is thus an object of the present invention to provide a unitary device which will allow for the recording of physical growth of one or more members of a family group and also provide for recording of significant events in the life of one or more members of a family group, all of which can be maintained in a convenient structure throughout the lifetime of either an individual or the collective life of a family group.

SUMMARY OF THE INVENTION

According to the present invention, a device for recording both chronological events and physical growth events of an individual or group of individuals' lives is provided. The device includes an extended linear measuring device having at least first and second opposed sides. The first side has a linear measurement scale inscribed thereon and at least one recording surface associated therewith. The measuring scale is preferably in feet and inches or meters and centimeters. The second side has a chronological scale, preferably in months and years, inscribed thereon and also has at least one recording surface associated with the chronological scale. Thus, physical growth can be measured on the first side and recorded on the recording surface associated therewith as the individual or several individuals grow physically. Significant events can be recorded on the other side such as, but not limited to, first walking steps, first words, first haircut, first day in school, graduation from school, entering a profession or trade, weddings, birth of children, and significant honors received, such as trophies from sporting events, academic awards, etc.

The device serves as a permanent record of an individual's life or the lives of a group, such as a family group, which can be collectively recorded on the surfaces, preferably by using a different colored marking for each individual in the group. Thus, a complete record of both chronological growth and occurrence of significant events in an individual's life, or group's life or lives collectively, can be maintained in a convenient format on a given single device which can stay with the individual or group for the life of the individual or the collective lifetime of the group.

DESCRIPTION OF THE PREFERRED EMBODIMENTS

Figure 1:
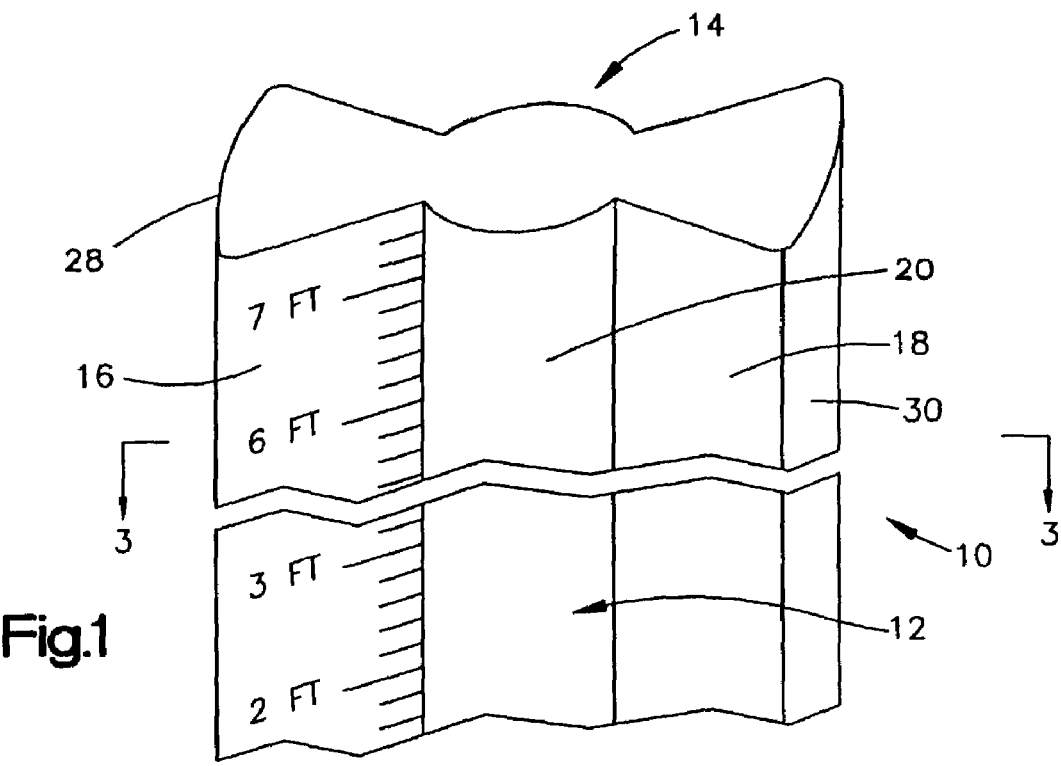
FIG. 1 in a perspective view of the obverse side of a measuring device according to this invention.
Figure 2:
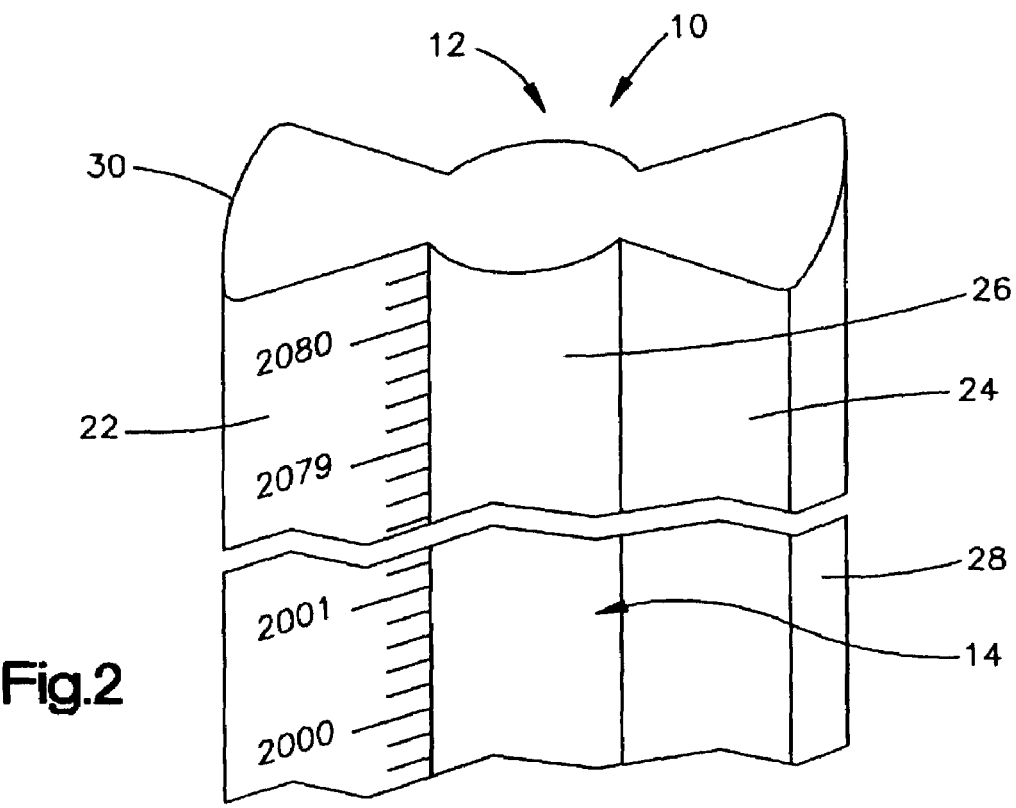
FIG. 2 is a perspective view similar to FIG. 1 of the reverse side of a measuring device according to this invention.
Figure 3:
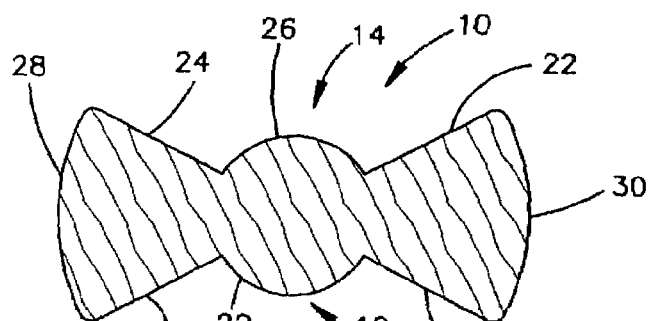
FIG. 3 is a sectional view taken substantially along the plain designated by the line 3—3 of FIG. 1.
Figure 3D:
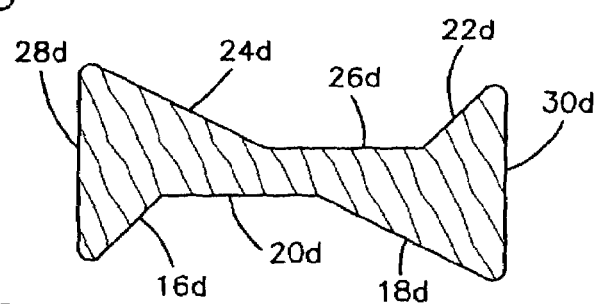
FIGS. 3a through 3k are various different configurations in cross-section of the device of FIG. 1.
Figure 3A:
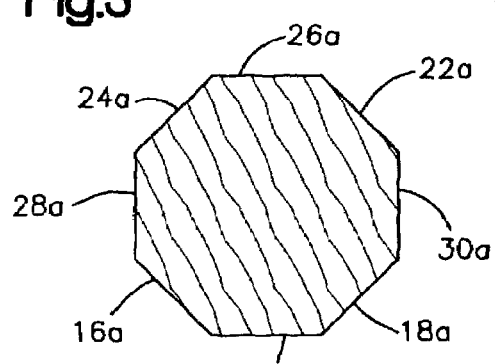

Referring now to the drawings and, for the present, to FIGS. 1, 2 and 3, one embodiment of a measuring device 10 according to the present invention is shown. The measuring device 10 is a rod-like structure, preferably approximately one to seven feet long (or slightly longer, depending upon the height of what is being measured), so that it can accommodate the full height of virtually all individual people, and having an effective diameter of between one and six inches. If the device is to measure the height of individuals other than people, such as animals, it can be longer or shorter, as will be described presently. The preferred shape of the measuring device is shown in FIGS. 1, 2 and 3. The measuring device 10 has a front or obverse side 12 and a rear or reverse side 14. Each of the sides preferably has three surfaces. The obverse side 12 has surfaces 16, 18 and 20. The surface 16 has engraved, or etched, or printed thereon, a linear measurement scale which preferably is in either feet and inches or meters and centimeters. In the illustrated embodiment, the measurement marks are etched in feet and inches and are used to measure the physical height of a person or persons, as will be described presently.

The reverse or rear side 14 has surfaces 22, 24, and 26. The surface 22 has etched or engraved therein a chronological scale. The chronological scale preferably is in years and months. This chronological scale can be chronological years in some particular calendar system, such as the Julian or the Gregorian calendars; however, other particular calendar systems could be used, such as the Hebrew or Confusion calendar, as well as other calendars. Alternatively, the chronological markings could start at the year "0" to correspond to the year of birth of a person or the eldest member of the family group and be scaled for time periods after that. Also, it is to be understood that while it is preferred that the markings for both the physical measurements and the chronological measurements be etched or engraved, other techniques could be employed, such as applying the markings in ink or by a transfer process or any other relatively permanent media on the surfaces 16 and 22.

The surface 20 on the obverse side is used to mark the height of an individual as that individual grows, and the surface 18 is used to record the date on which this height was reached or any other significant information relative thereto. It is to be understood, however, that if the measuring device tends to be used for multiple individuals, such as a family group, the measurement for each person can be done in a distinctive way, such as by different color ink or markings or by different configurations of the marking. However, the preferred way is by different colors if the rod is to be used for multiple individuals, such as a portion of or a total family group.

Similarly, chronological achievements can be recorded on the surface 26 of the reverse side. As indicated earlier, these chronological milestones, or achievements, can include such things as first steps, starting to talk, starting school, graduation from various schools, achievements and honors, such as sport achievements or other achievements, and awards for excellence in particular fields, and these events continue for a lifetime. These particular achievements are marked on the surface 26 with a line which will correspond to the chronological markings on surface 22, and the surface 24 can be used to indicate what these achievements are or indeed even mount mementos of such achievements thereon by means of a thumbtack or the like.

In order to have the measuring device amenable to mounting of various mementos thereon, the measuring device preferably should be made, at least in part, of wood, cork, or other material which is amenable to having such mementos attached. An example of such mementos could include something to signify a wedding, or possibly a baby charm engraved with a name to signify the birth of a child or grandchild, or trophy ribbons or tassels from a graduation cap. Indeed, the things that can be commemorated on the reverse side for chronological achievements are limited only by the imagination of the person using the device. However, the attachment of such mementos is not required and the mere marking of the event chronologically on the surface 26 corresponding with the chronological time on the surface 22, together with a brief description on the surface 24, may suffice.

Opposite side surfaces 28 and 30 can either be pre-ornamented with some kind of design, or engraved with a personal name or family name or, more preferably, can be left plain for the person who is being measured by the device 10 to put different ornamentation and adornments on the side corresponding to either chronological or physical locations on the device, or just random designs as the device is being used. In any event, one side 12 is used for measuring physical growth and the other side 14 is used for measuring chronological achievements, all in a single device which can be retained through the lifetime of the individual or, if the device is being used for recording the events of a family group, can be retained for the collective life of the family group as a relatively permanent record of both physical growth and chronological achievements. It will also be noted that in this embodiment the surfaces 16, 18, 20, 22, 24, and 26 are recessed from the arc subtended by the surfaces 28 and 30. This allows one to grasp the device by surfaces 28 and 30 without having to touch surfaces 16, 18, 20, 22, 24, and 26, thus preventing them from sustaining unintended soiling and wear. This is especially desirable for surfaces 18, 20, 24, and 26.

Figure 3E:
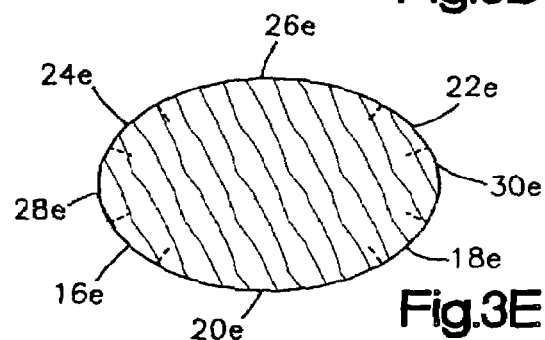
Figure 3B:
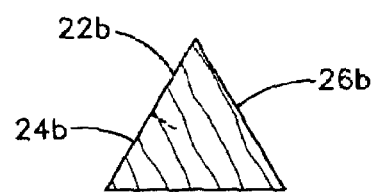
Figure 3C:
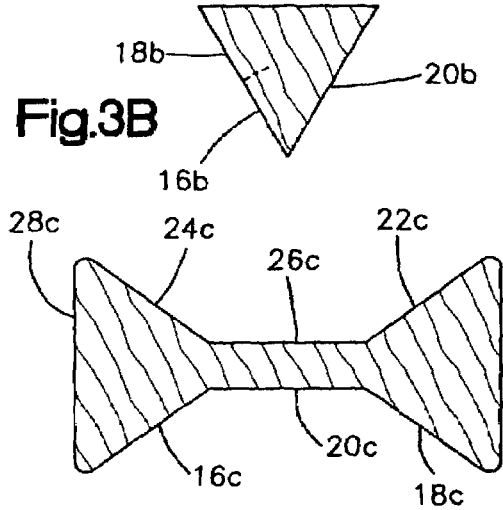
Figure 3F:
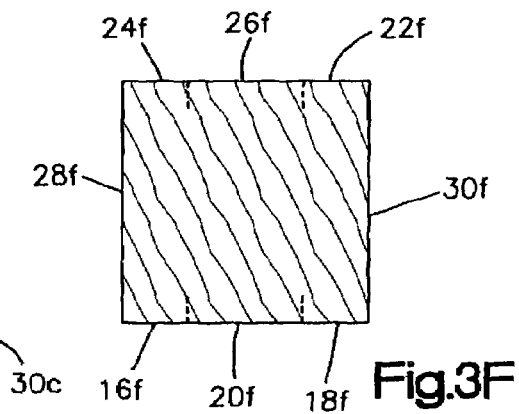
Figure 3G:
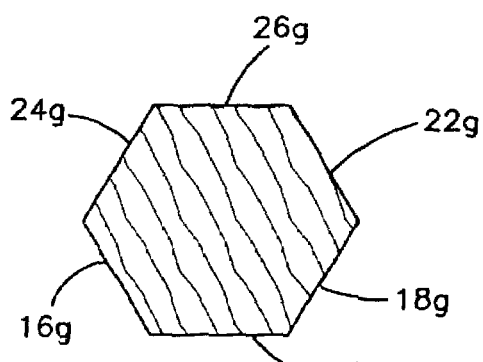
Figure 3J:
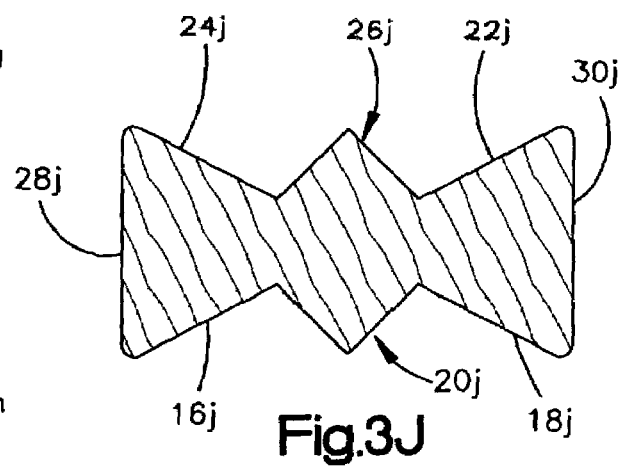
Figure 3H:
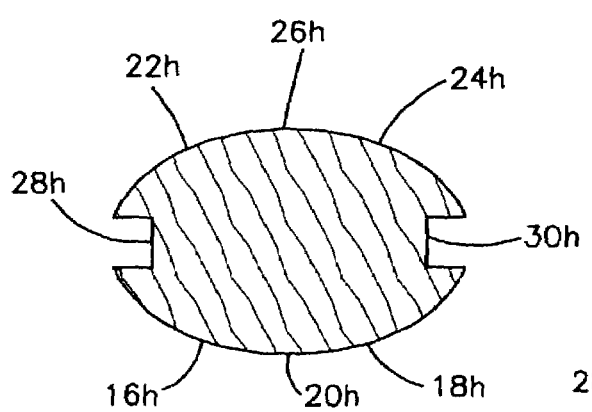
Figure 3K:
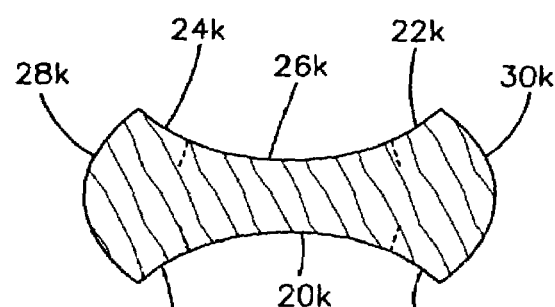
Figure 3I:
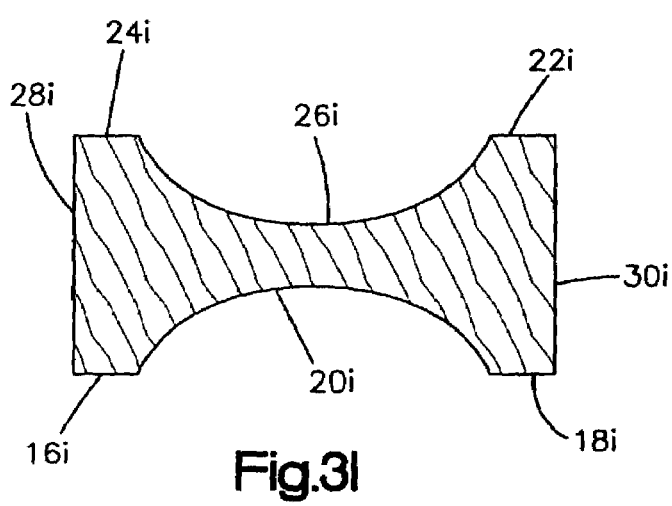

It is, of course, to be understood that FIGS. 1, 2, and 3 are representative of merely one cross-sectional configuration of a device that could be used. FIGS. 3*a* through 3*k* show different cross-sectional configurations that could be employed. These configurations include polyhedrons, hourglass, modified hourglass, round, non-cordal round, and some free form shapes. The important thing is that one side be provided with markings thereon for physical growth and another side be provided with markings thereon for chronological achievements, with space on both sides to make markings to indicate the corresponding physical or chronological time, and a space to record information relating thereto or for attaching information relating thereto. It is to be understood that in some cases the opposite sides will be merely the two different 180° arcs of a circle and that the surfaces would be lesser arcs of each of the 180° arcs of the circle, as shown in FIG. 3*e*. Or, as shown in FIG. 3*f*, the sides could be a square with the angled part oriented outwardly and the markings on a portion of one face, or the indicia or chronological order measurement indicia on the portion of one face, with room to mark adjacent thereto on the same face while the other face has the portion for description. In any event, measuring faces are denoted by the reference character 16 followed by its letter suffix carrying to the beginning number. This reference scheme is carried out for surfaces 18, 20, 22, 24, and 26.

Figure 5A:
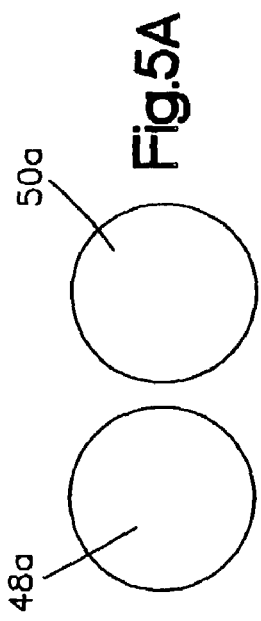
FIGS. 5a through 5c are sectional views of the rotatively mounted shafts of FIG. 4.
Figure 5B:
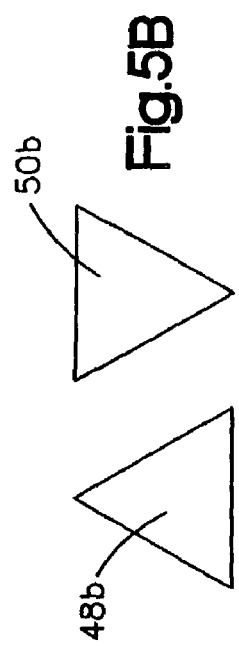
Figure 5C:
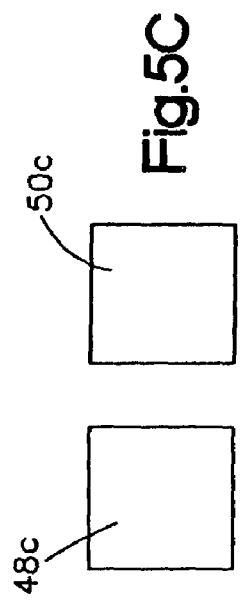
Figure 4:
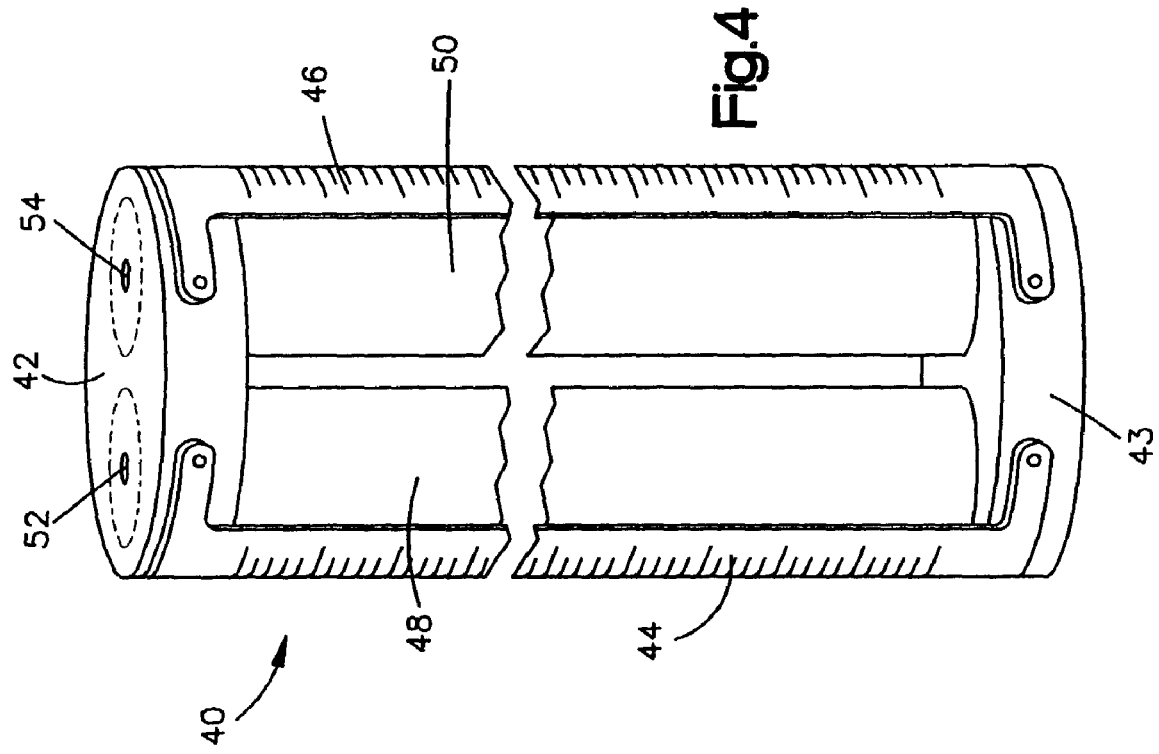
FIG. 4 is perspective view of another embodiment of the device according to the present invention.

Referring now to FIG. 4, another embodiment of the present invention is shown. In this embodiment, the device 40 includes a pair of end members 42 and 43 mounted by two scaling members 44, 46. A pair of rotatively mounted members 48 and 50 is mounted on axels 52 and 54 extending between end members 42, 43 so as to rotate freely. The rotatively mounted members 48 and 50 can have different cross-sectional configurations, as shown in FIGS. 5*a*, 5*b* and 5*c* and designated with the letter suffixes corresponding to the figure designation. The rotational members 48 and 50 are used to record markings of physical or chronological events and, preferably, each scaling member 44, 46 has formed either the linear scale of feet and inches or similar markings, or the chronological scale so that the rotatable members 48 and 50 can be rotated to match up with either scaling member. Alternatively, the rotatable member could be marked, as with chronological markings, and the other with linear markings, and the scaling member used for ornamentation or engraving or the like. It is also to be understood that the end caps 42 and 43 could be engraved with different types of decorative work in the original condition or can be used to allow such art work to be engraved as the device is being used.

The device is principally intended to measure human growth and to record human achievements; however, the device can be used for the same purposes for animals, such as dogs and horses. Hence, depending upon the animal being measured, the length can be more than seven feet and, even in some cases, less than one foot. But for human beings, seven feet is about right.

What is claimed is:

1. A device for measuring and recording both chronological events and physical growth events in an individual's life comprising:

an elongated rod-like structure comprising a measuring and recording device having a front and reverse side;

said elongated rod-like structure includes an extended linear measuring device having at least a front side and a reverse side, said front side of said extended linear measuring device having a linear scale measurement for measuring physical growth inscribed thereon and at least one recording surface associated therewith; and said reverse side of said extended linear measuring device having a chronological scale inscribed thereon wherein the chronological scale is comprised of calendar year markings and at least one recording surface associated therewith.

2. The device as defined in claim 1 wherein said elongate rod-like structure is a unitary pole.

3. The device as defined in claim 2 wherein said recording surfaces are each recessed.

4. The device as defined in claim 2 wherein each said linear scale and chronological scale are inscribed on a surface separate from the recording surface associated therewith.

5. The device as defined in claim 2 wherein said front and reverse sides of said extended linear measuring device are opposite each other.

6. The device as defined in claim 1 wherein the surfaces of the front and reverse sides of said extended linear measuring device are curvilinear.

7. The device as defined in claim 1 wherein said front and reverse sides of said extended linear measuring device include flat surfaces.

8. The device as defined in claim 1 wherein the shape of the rod-like structure in cross-section includes a polyhedral shape.

9. The device as defined in claim 1 wherein the device is at least seven feet tall.

10. The device as defined in claim 1 wherein the linear scale is in English or metric units.

11. The device as defined in claim 1 wherein the chronological scale is in Julian or Gregorian units.

12. The device according to claim 1 having a cross-sectional configuration selected from the group consisting of polyhedrons, hourglass, modified hourglass, round, and noncordal round shape.

13. A device for measuring and recording both chronological events and physical growth events in an individual's life comprising:

an elongated rod-like structure comprising a measuring and recording device having a front and reverse side;

said elongated rod-like structure includes an extended linear measuring device having at least a front side and a reverse side, said front side of said extended linear measuring device having a linear scale measurement for measuring physical growth inscribed thereon and at least one recording surface associated therewith;

said reverse side of said extended linear measuring device having a chronological scale inscribed thereon and at least one recording surface associated therewith; and wherein said rod-like structure includes first and second independently mounted rods.

14. The device as defined in claim 13 wherein each rod is mounted for individual rotation.

15. The device as defined in claim 13 further characterized by a rod support structure mounting said rods in parallel.

* * * * *